United States Patent
Ueno

(10) Patent No.: US 9,075,940 B2
(45) Date of Patent: Jul. 7, 2015

(54) SIMULATION METHOD FOR HIGH POLYMER MATERIAL

(71) Applicant: SUMITOMO RUBBER INDUSTRIES, LTD., Kobe-shi, Hyogo (JP)

(72) Inventor: Shinichi Ueno, Kobe (JP)

(73) Assignee: SUMITOMO RUBBER INDUSTRIES, LTD., Kobe-Shi (JP)

(*) Notice: Subject to any disclaimer, the term of this patent is extended or adjusted under 35 U.S.C. 154(b) by 286 days.

(21) Appl. No.: 13/758,096

(22) Filed: Feb. 4, 2013

(65) Prior Publication Data

US 2013/0238302 A1 Sep. 12, 2013

(30) Foreign Application Priority Data

Mar. 8, 2012 (JP) ................. 2012-052063

(51) Int. Cl.
*G06F 17/50* (2006.01)
*G06F 19/00* (2011.01)

(52) U.S. Cl.
CPC .......... *G06F 17/5009* (2013.01); *G06F 19/701* (2013.01); *G06F 19/704* (2013.01)

(58) Field of Classification Search
USPC ...................................... 703/2, 5, 6
See application file for complete search history.

(56) References Cited

U.S. PATENT DOCUMENTS

| | | | |
|---|---|---|---|
| 8,924,188 B2 * | 12/2014 | Ueno | 703/2 |
| 2010/0303874 A1 * | 12/2010 | Akcora et al. | 424/401 |
| 2013/0238302 A1 * | 9/2013 | Ueno | 703/6 |

FOREIGN PATENT DOCUMENTS

JP  2006-64658 A  3/2006

* cited by examiner

*Primary Examiner* — Thai Phan
(74) *Attorney, Agent, or Firm* — Birch, Stewart, Kolasch & Birch, LLP

(57) ABSTRACT

A computerized simulation method for evaluating dispersion of fillers in a high polymer material is disclosed, wherein the simulation step includes a link step in which filler particles which are approached to less than a predetermined distance to polymer particles, are linked to the polymer particles. The filler particles constituting each filler model are a single center filler particle and at least four surface filler particles of which centers are positioned on a spherical surface of which center coincides with the center of the center filler particle. Between the center filler particle and the surface filler particles and also between the surface filler particles, equilibrium lengths are respectively defined. The polymer particles can be linked to only the surface filler particles.

9 Claims, 13 Drawing Sheets

SIMULATION METHOD FOR HIGH POLYMER MATERIAL

BACKGROUND OF THE INVENTION

The present invention relates to a simulation method for a high polymer material useful for evaluating or improving filler dispersion and capable of improving the accuracy of simulation.

High polymer materials such as compounded rubber used in vehicle tires usually contain fillers such as carbon black and silica. It is well known in the art that the dispersion of fillers in a compounded rubber exerts a strong influence on properties, e.g. strength of the rubber.

In recent years, in order to evaluate the dispersion of fillers in a high polymer material, various computerized simulation (numerical calculation) methods have been proposed. For example, Japanese Patent Application Publication No. 2006-64658 discloses this kind of simulation method, wherein, as shown in FIG. 13(a), a filler model (a) representing a single filler particle (a1) and a polymer model (b) representing a plurality of polymer particles (b1) are defined, and then a molecular dynamics (MD) calculation is made for the filler models (a) and polymer models (b) placed or set in a predetermined virtual space.

In this simulation method, due to the filler model (a) which represents a single filler particle (a1), when the polymer model (b) is coupled to the filler particle (a1), as shown in FIG. 13(b), the position of the polymer model (b) relative to the filler model (a) is hard to be settled uniquely, and the polymer model (b) makes a sliding movement on the surface of the filler model (a) (or a turning movement around the filler model (a)). Thus, it is difficult to obtain accurate simulation results.

SUMMARY OF THE INVENTION

It is therefore, a primary object of the present invention to provide a simulation method for a high polymer material, in which the sliding movement or turning movement of the polymer model can be avoided, and by which accurate simulations of fillers dispersing in the high polymer material are possible, and thus which is very useful for evaluating or improving the filler dispersion.

According to the present invention, a computerized simulation method for evaluating dispersion of fillers in a high polymer material, comprises a filler model defining step in which filler models of the fillers are defined, wherein each of the filler models represents filler particles, a polymer model defining step in which polymer models of the high polymer material are defined, wherein each of the polymer models represents polymer particles, a condition setting step in which simulation conditions are set, a simulation step in which a molecular dynamics calculation is made for the polymer models and the filler models placed in a virtual space, and an evaluation step in which the dispersion of the filler models is evaluated from data obtained in the simulation step by the molecular dynamics calculation, wherein the filler particles of each of the filler models are a single center filler particle and at least four surface filler particles of which centers are positioned on a spherical surface of which center coincides with the center of the center filler particle, between the center filler particle and the surface filler particles and also between the surface filler particles, equilibrium lengths are respectively defined, and the simulation step includes a link step in which the filler particles, which are approached to less than a predetermined between-particle distance to the polymer particles, are linked to the polymer particles under such conditions that the polymer particles can be linked to only the surface filler particles.

Therefore, according to the present invention, the filler model is formed in a polyhedral shape where the center filler particle and the surface filler particles are mutually linked so as to maintain their relative positions, and the polymer particles link to only the surface filler particles. As a result, the position of the polymer model relative to the filler model becomes settled uniquely not to cause the sliding movement of the polymer model. Thus, it is possible to estimate the state of dispersion of the filler models in relation to the polymer models, and the simulation accuracy can be improved.

The computerized simulation method according to the present invention may be further provided with the following features (A)-(G):

(A) between the filler particles and the polymer particles, potentials are defined so that when the distance between the concerned particles is decreased under a predetermined cutoff distance, a mutual interaction occurs therebetween, and the cutoff distance related to the center filler particle is larger than the sum of the cutoff distance related to the surface filler particle and the radius of the spherical surface;

(B) the evaluation step includes a step of computing a radial distribution function for the center filler particle of each of the filler models;

(C) the shape of the virtual space is a regular hexahedron, the distance range of the radial distribution function is from zero to one half of the length of one side of the shape of the virtual space, and acquisition intervals of the radial distribution function correspond to a distance of not more than ⅕ times said one half of the length;

(D) the condition setting step includes an initial setup step in which the filler models and the polymer models are placed in the virtual space, and a compact cluster defining step in which a compact cluster of at least two filler models is formed by approximating the filler models so as to cause a mutual interaction between the filler models;

(E) the simulation step includes a filler movement limiting step in which movement of each of the filler particles is limited, a polymer calculation step in which a molecular dynamics calculation is made for each of the polymer models, excluding the filler particles, a releasing step in which the filler particles are released, and a filler-and-polymer calculation step in which a molecular dynamics calculation is made for the filler models and the polymer models;

(F) in the polymer calculation step, when the molecular dynamics calculation is made in steps of approximate $0.05[\tau]$, the number of the steps is 100 or more; and (G) in the filler-and-polymer calculation step, when the molecular dynamics calculation is made in steps of approximate $0.05[\tau]$, the number of the steps is 1000 or more.

DESCRIPTION OF THE PREFERRED EMBODIMENT

An embodiment of present invention will now be described in detail in conjunction with accompanying drawings.

The simulation method according to the present invention is a computerized method for evaluating the dispersion of fillers in a high polymer material by the use of a computer 1. Here, the term "high polymer material" is intended to include at least rubber, resin and elastomer. The term "filler" is intended to include at least carbon black, silica and alumina.

Figure 1:
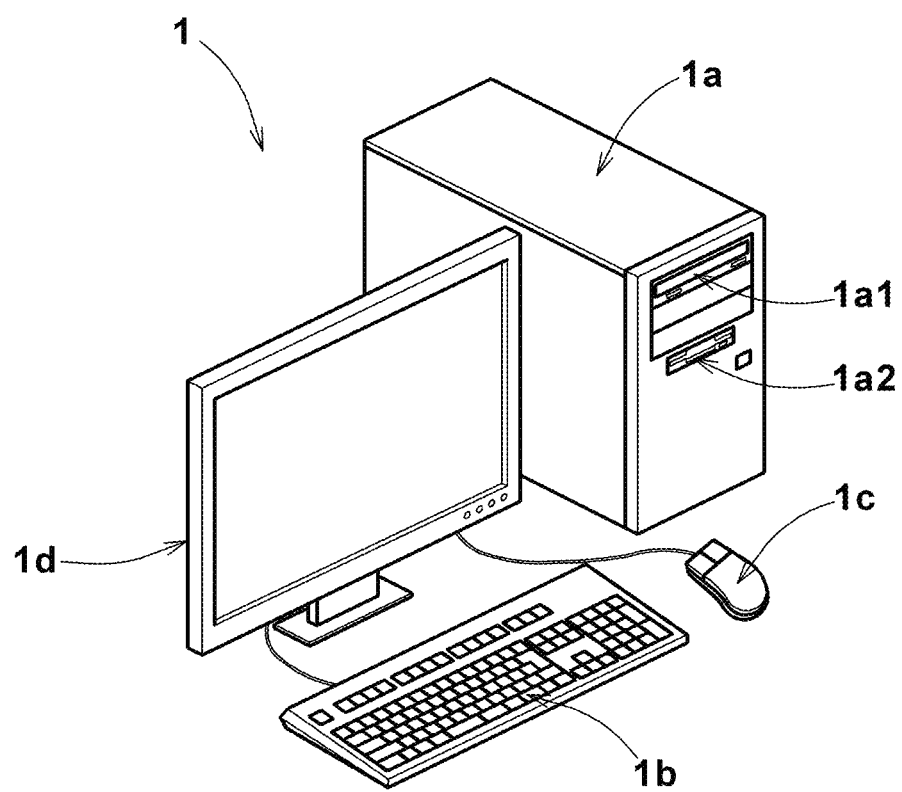
FIG. 1 is a perspective view of a computer system implementing a simulation method as an embodiment of the present invention.

As shown in FIG. 1 for example, the computer 1 comprises a main body 1a, a keyboard 1b, a mouse 1c and a display 1d. The main body 1a comprises an arithmetic processing unit (CPU), ROM, work memory, storage devices such as magnetic disk, disk drives 1a1 and 1a2 and the like. In the storage device, programs/software for carrying out the simulating method are stored.

Figure 2:
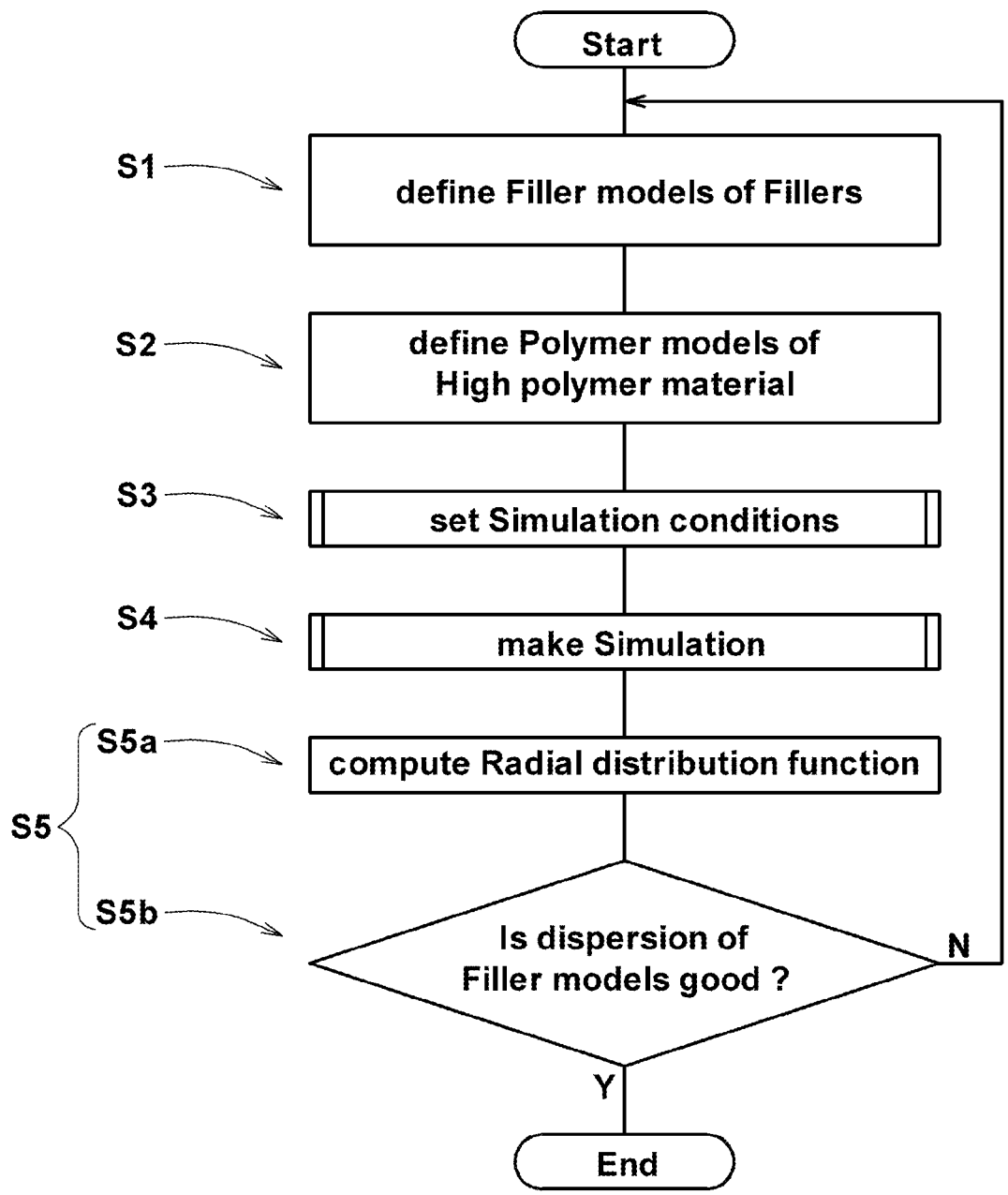
FIG. 2 is a flow chart of the simulation method in this embodiment.

FIG. 2 shows a flowchart of the simulation method as an embodiment of the present invention, wherein the simulation method comprises a filler model defining step S1 in which filler models 3 of the fillers are defined, a polymer model defining step S2 in which polymer models 5 of the high polymer material are defined, a condition setting step S3 in which simulation conditions are set, a simulation step S4 in which a molecular dynamics calculation is made, an evaluation step S5 in which the state of dispersion of the filler models 3 is evaluated.

Figure 3:
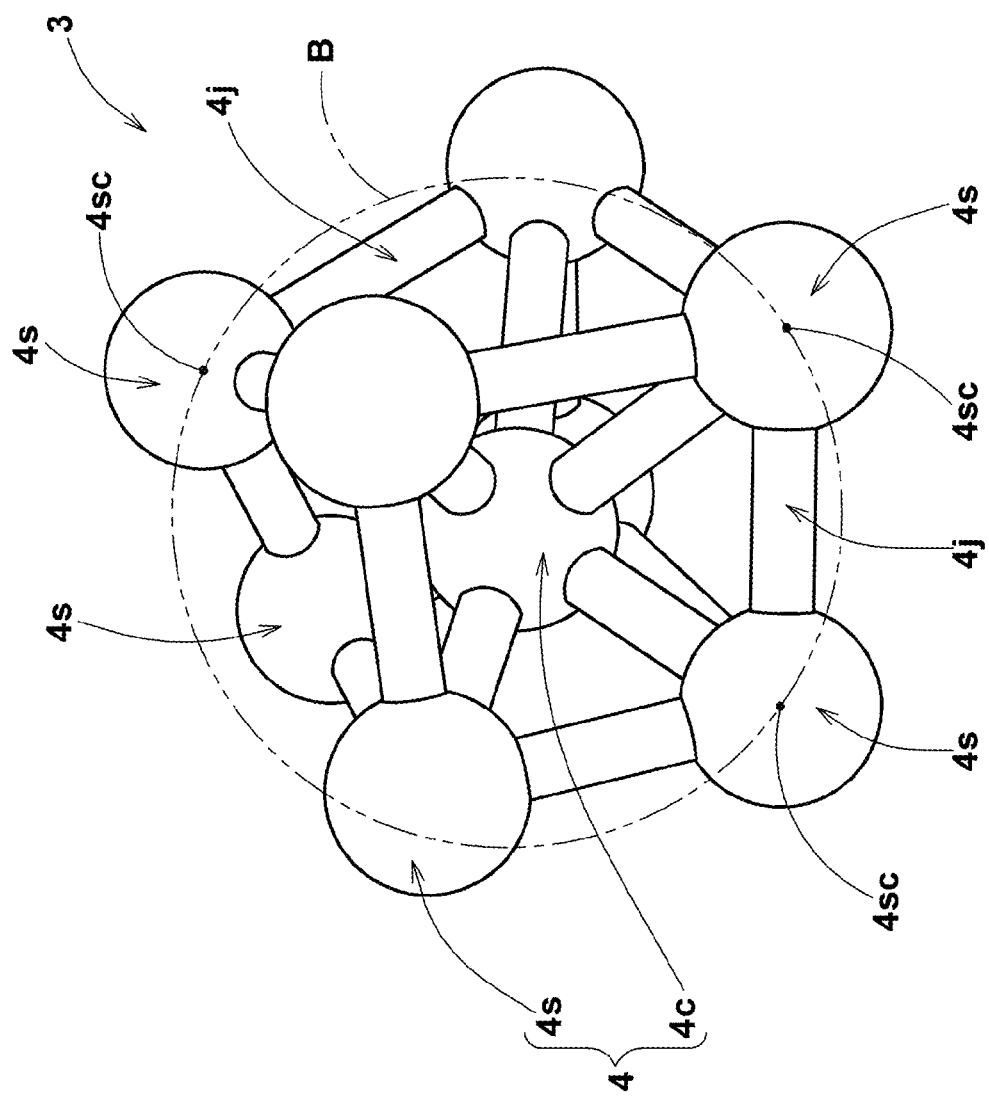
FIG. 3 is a diagram showing a filler model.

In the filler model defining step S1, as shown in FIG. 3, each filler model 3 is defined to represent a plurality of filler particles 4, wherein each of the filler particles 4 is a sphere having a certain diameter.

The filler particles 4s constituting each filler model 3 are a single center filler particle 4c, and at least four in this example eight surface filler particles 4s, wherein the centers 4sc of the surface filler particles 4s are positioned on a spherical surface B of which center coincides with the center of the center filler particle 4c.

Incidentally, the filler model 3 corresponds to numerical data (inclusive of the mass, volume, diameter and initial coordinates of each of the filler particles 4) necessary to deal with the fillers by the molecular dynamics. Such numerical data are entered and stored in the computer 1.

Between the center filler particle 4c and the surface filler particles 4s and also between the surface filler particles 4s, there are provided joining chains 4j on which equilibrium lengths are respectively defined.

Here, the equilibrium lengths are the bond distances between the center filler particle 4c and the surface filler particles 4s and between the surface filler particles 4s when the relative positions of the surface filler particle 4s on the spherical surface B become steady.

Further, the center filler particle 4c and three or more surface filler particles 4s are arranged so as not to locate in the same plane or one plane.

In the filler model 3 in this example, the center filler particle 4c and the surface filler particles 4s are bonded, keeping their relative positions. The surface filler particles 4s are positioned at the vertices of a polyhedron, and the center filler particle 4c is positioned at the center of the polyhedron.

Figure 4:
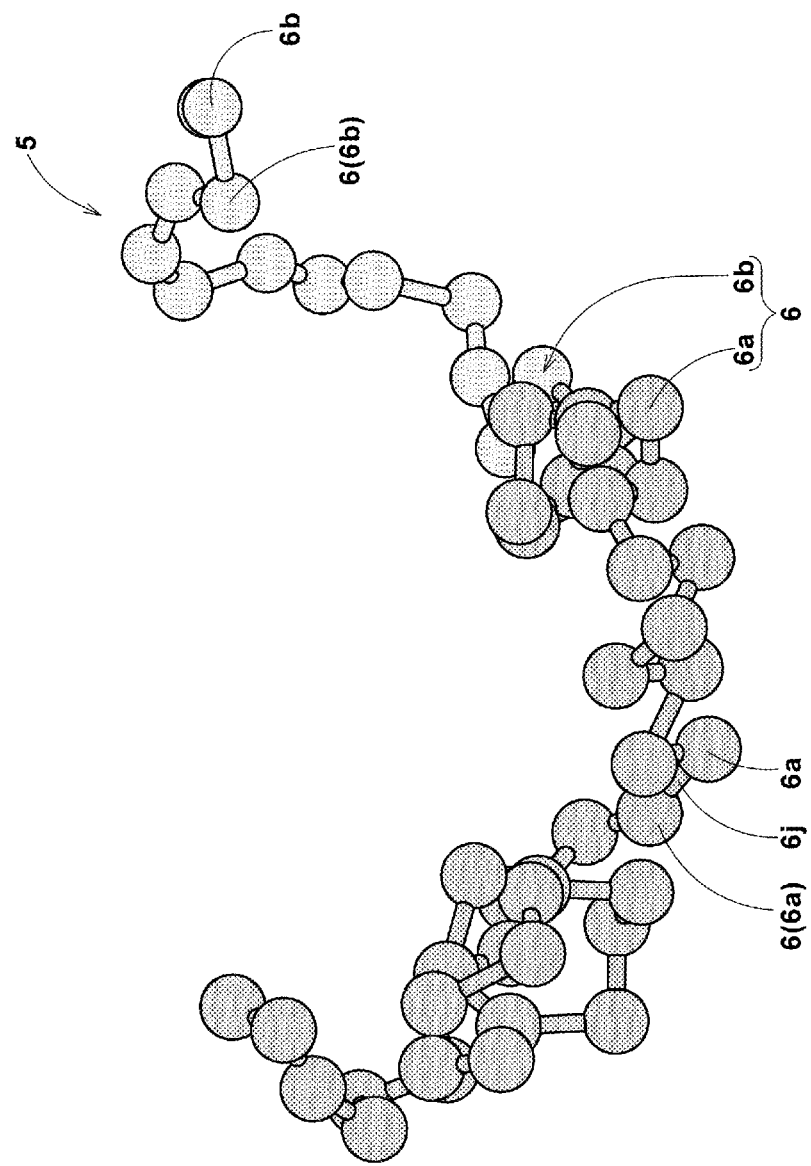
FIG. 4 is a diagram showing a polymer model.

In the polymer model defining step S2, as shown in FIG. 4, each polymer model 5 is defined to represent a number of polymer particles 6 of the high polymer material.

The polymer model 5 corresponds to numerical data necessary to deal with the high polymer material by the molecular dynamics. Such numerical data are entered and stored in the computer 1.

The polymer particles 6 of the polymer model 5 in this embodiment include modified basal particles 6b and non-modified particles 6a on which different potentials (after-mentioned) are defined. Each of the particles 6a and 6b is a sphere having a certain diameter.

Between the particles 6a and 6b, there are provided joining chains 6j so as to keep them under restraint and to have a three dimensional structure like a straight-chain polymer.

Figure 5:
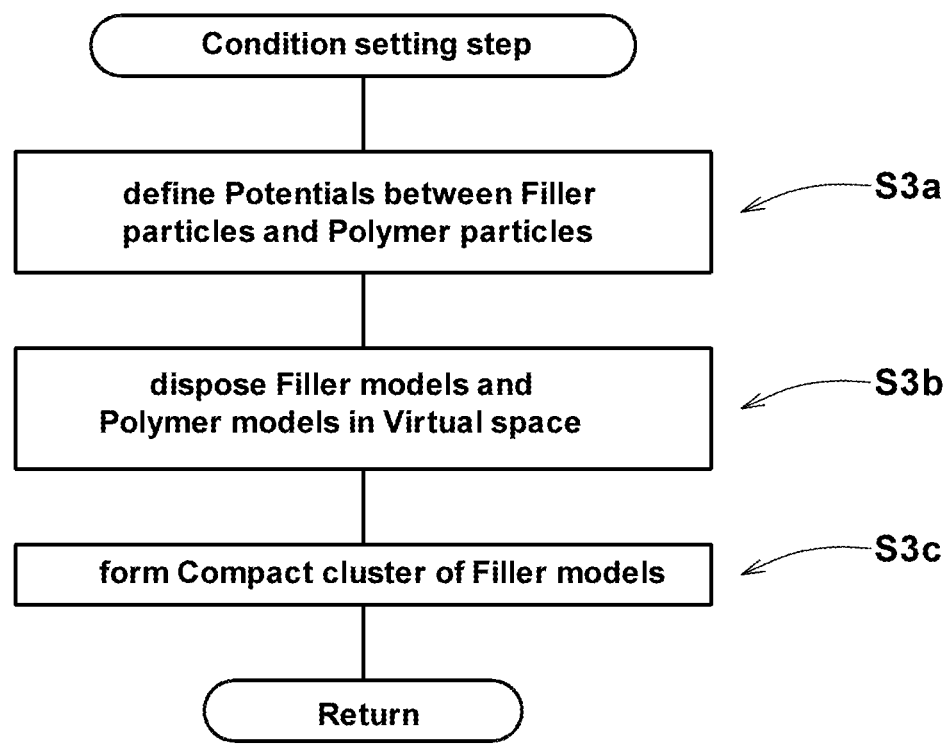
FIG. 5 is a flow chart of a condition setting step.

FIG. 5 shows a flow chart of the condition setting step S3 in this embodiment.

In the condition setting step S3 in this embodiment, firstly, a potential defining step S3a is implemented.

Figure 6:
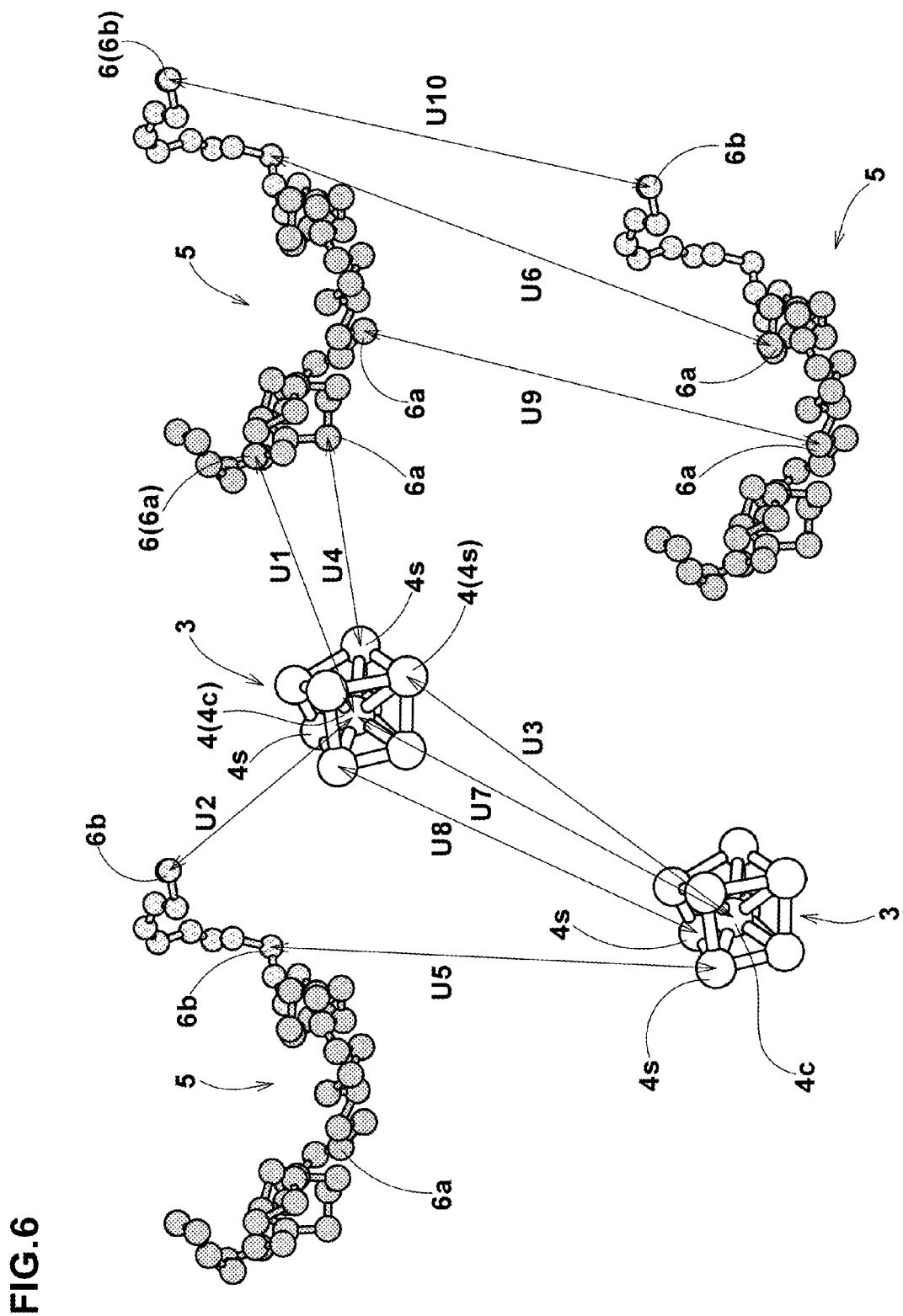
FIG. 6 is a diagram for explaining potentials of the filler particles and polymer particles.

In the potential defining step S3a, as shown in FIG. 6, between the filler particles 4c,4s and polymer particles 6a,6, potentials are respectively defined.

The potentials are entered and stored in the computer 1 as numerical data, and used to calculate a force between the two particles.

Here, the potential is a function of the distance between the concerned particles. The potential is given by the following expression (1):

$$U = \frac{1}{2} a_{ij} \left(1 - \frac{r_{ij}}{r_c}\right)^2$$

wherein $a_{ij}$ is the strength of the potential defined between the particles concerned, $r_{ij}$ is the distance between the centers of the particles concerned, and $r_c$ is the cutoff distance predetermined between the centers of the particles concerned.

with the expression (1), the potential is defined such that a mutual interaction (in this embodiment, a repulsive force) occurs if the distance $r_{ij}$ is decreased under the cutoff distance $r_c$. If the distance $r_{ij}$ is more than the cutoff distance $r_c$, the potential U is zero and no repulsive force occurs between the particles.

In this particular example, for the following combinations of two particles, potentials U1-U10 are defined:
- particles 4c-6a: potential U1
- particles 4c-6b: potential U2
- particles 4c-4s: potential U3
- particles 4s-6a: potential U4
- particles 4s-6b: potential U5
- particles 6a-6b: potential U6
- particles 4c-4c: potential U7
- particles 4s-4s: potential U8
- particles 6a-6a: potential U9
- particles 6b-6b: potential U10

As to the strength $a_{ij}$ of the potential, a treatise (J. Chem Phys. 107(11) 4423-4435 (1997)) proposes that the strength $a_{ij}$ of potential between particles of the same kind is set to be 25. But, various researches made afterward (for example, Macromolcule vol. 39 6744 (2006)) suggest that the strength $a_{ij}$ of potential between particles of the same kind is set to be 50, and the strength $a_{ij}$ of potential between particles of the different kinds is set to be 72.

In this example, by reference to these values, the strength $a_{ij}$ of the potentials U1-U10 are set as follows.
- potential U1: $a_{ij}=72$
- potential U2: $a_{ij}=25$
- potential U3: $a_{ij}=50$
- potential U4: $a_{ij}=72$
- potential U5: $a_{ij}=25$
- potential U6: $a_{ij}=72$
- potential U7: $a_{ij}=50$
- potential U8: $a_{ij}=50$
- potential U9: $a_{ij}=50$
- potential U10: $a_{ij}=50$ As above, the strength $a_{ij}$ (=25) of the potential U2,U5 between the modified basal particle 6b of the polymer model 5 and the filler particle 4c,4s of the filler model 3 is set to be smaller than the strength $a_{ij}$(=72) of the potential U1,U4 between the nonmodified particle 6a of the polymer particle 6 and the filler particle 4c,4s of the filler model 3, therefore, in comparison with the nonmodified particle 6a, the modified basal particle 6b is decreased in the repulsive force. Such modified basal particle 6b is increased in the affinity to the filler particle 4c,4s, and therefore can simulate a denaturizing agent actually added in the high polymer material. Accordingly, by incorporating such modified basal particles 6b in the polymer model 5, the dispersion of the filler models 3 in the polymer models 5 can be changed, and it becomes possible to simulate a modified polymer.

Figure 7:
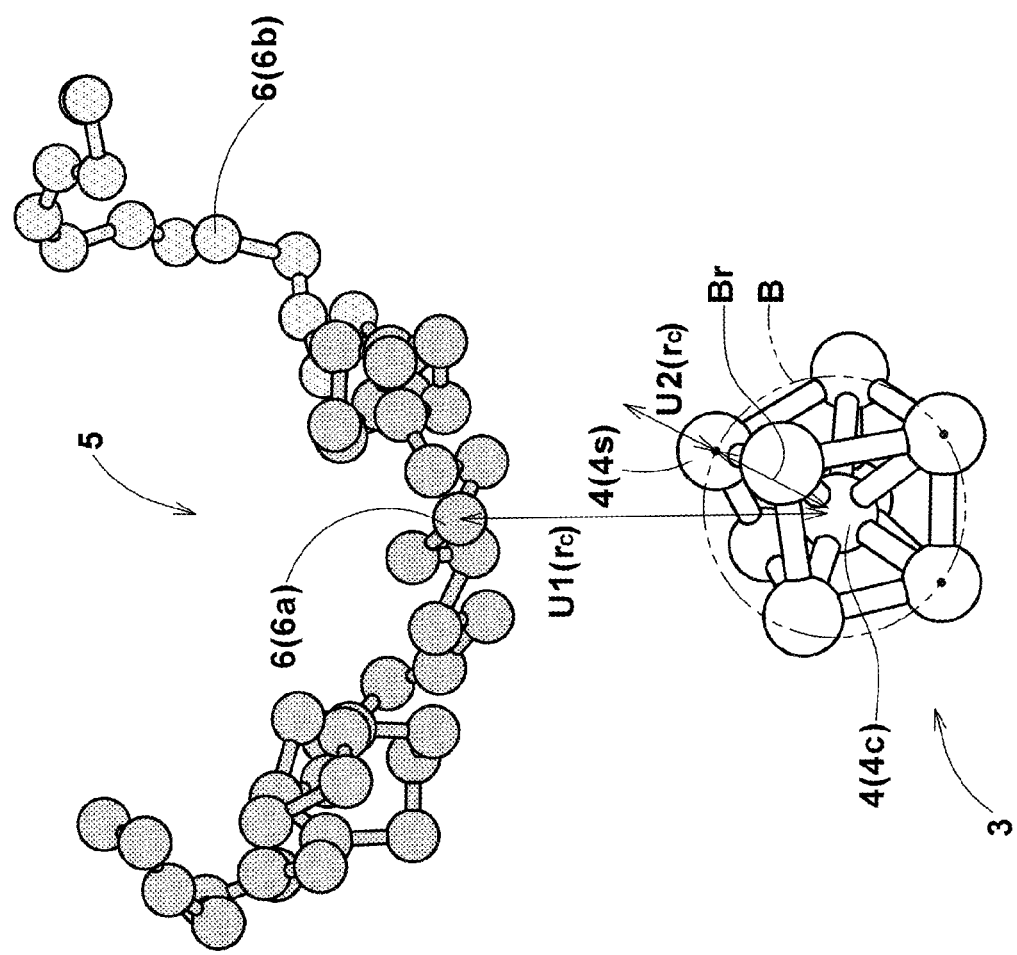
FIG. 7 is a diagram for explaining the cutoff distance of a filler particle.

In the expression (1), the cutoff distance $r_c$ is defined for each of the potentials U1-U10 as follows.
- potential U1: $r_c=3$
- potential U2: $r_c=3$
- potential U3: $r_c=3$
- potential U4: $r_c=1$
- potential U5: $r_c=1$
- potential U6: $r_c=1$
- potential U7: $r_c=5$
- potential U8: $r_c=1$
- potential U9: $r_c=1$
- potential U10: $r_c=1$ As shown in FIG. 7, the cutoff distance $r_c$ of the potential (for example U1) related to the center filler particle 4c of the filler model 3 is set to be larger than the cutoff distance $r_c$ of the potential (for example, U4) related to the surface filler particles 4 of the filler model 3.

By defining the cutoff distance $r_c$ as above, the filler model 3 can exert the potentials U1 to U3 and U7 related to the center filler particles 4c preferentially than the potentials U4, U5 and U8 related to the surface filler particles 4s.

Further, since the center filler particle 4c is defined by a sphere having a certain diameter, the potential U1 to U3 and U7 can be defined to act radially. Therefore, in the molecular dynamics calculation, the computer 1 can deal with the filler model 3 as being a sphere, and the simulation accuracy can be improved.

Furthermore, the computer 1 can make the molecular dynamics calculation with respect to the filler model 3 by the use of the potentials of the center filler particles 4c and some of the surface filler particle 4s approached to under the cutoff distance $r_c$ if any, namely, by the use of substantially the potentials U1 to U3 and U7 of only the center filler particles 4c. Therefore, the computational efficiency can be improved.

In the condition setting step S3 in this embodiment, an initial setup step S3b is implemented by the computer 1.

Figure 8:
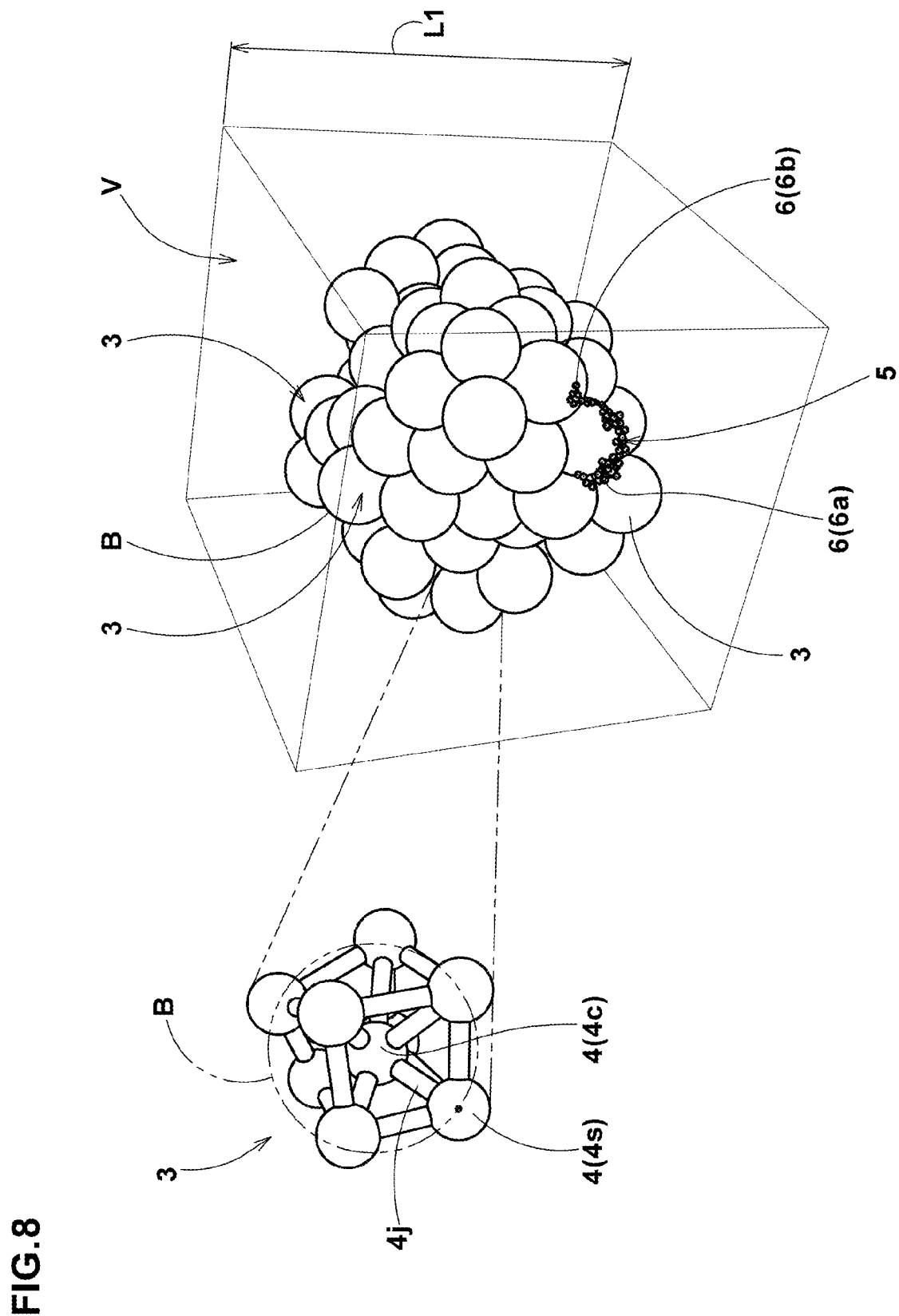
FIG. 8 is a perspective diagram for explaining a virtual space of a simulation model.

In the initial setup step S3b, as shown in FIG. 8, the filler models 3 and the polymer models 5 are disposed in the virtual space V having a predetermined volume, The virtual space V corresponds to a minute fraction of the actual rubber polymer as the analysis object.

In this embodiment, the shape of the virtual space V is a regular hexahedron whose each side has a length L1 of for example 30[σ]. [σ] is unit of length.

In the virtual space V, for example, one hundred filler models 3 and one thousand and five hundred polymer models 5 are initially, randomly disposed.

Next, a compact cluster defining step S3c is implemented by the computer 1.

In the compact cluster defining step S3c, a compact cluster of at least two filler models 3 is formed or defined by approximating the filler models 3 so as to cause a mutual interaction, in other words, by decreasing the distance between the concerned filler models under the cutoff distance $r_c$ defined therebetween.

Therefore, the compact cluster of the fillers which is liable to occur in the actual rubber polymer as the analysis object can be simulated in the virtual space V, and it becomes possible to make a simulation close to the real.

Figure 9:
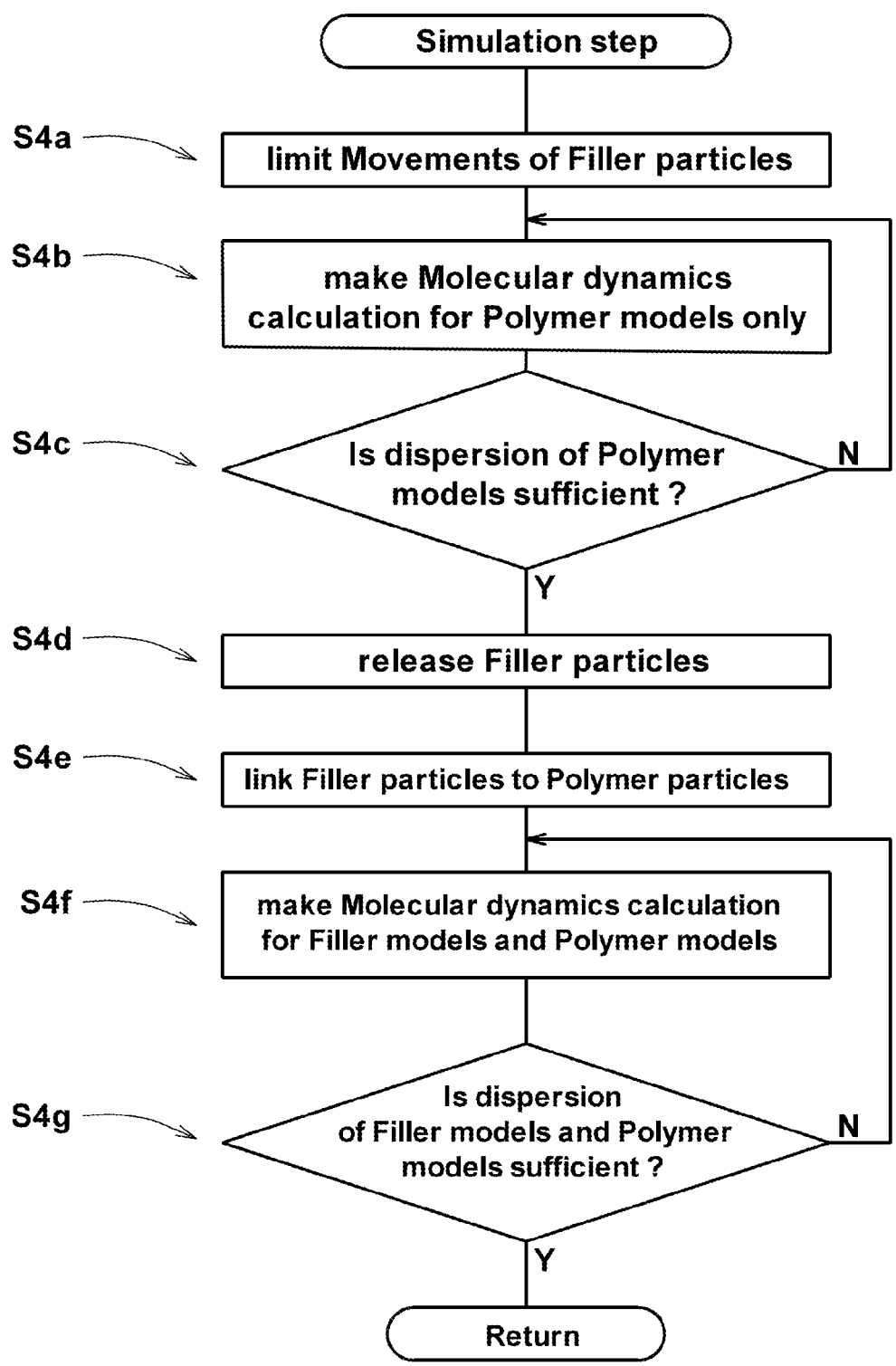
FIG. 9 is a flow chart of the simulation step in this embodiment.

FIG. 9 shows a flowchart of the above-mentioned simulation step S4 in this embodiment.

In the simulation step S4, firstly, a filler movement limiting step S4a is implemented by the computer 1.

In the filler movement limiting step S4a, movement of each of the filler particles 4c and 4s is limited. More specifically, by the computer 1, the positional coordinates of the filler particles 4 of each filler model 3 in the virtual space V are fixed relatively to the virtual space V in order to make the filler models 3 immovable in the next polymer calculation step S4b.

Next, the polymer calculation step S4b is implemented by the computer 1.

In the polymer calculation step S4b, only for the polymer models 5 in the virtual space V, the molecular dynamics calculation is made by the computer 1.

More specifically, assuming that all of the polymer models 5 (excluding all of the fixed filler models 3) follow the classical dynamics, the calculation according to Newton's equation of motion is made about the defined virtual space V during a given time period, and the motion of each of the polymer particles 6a and 6b is tracked at each time step during the time period.

During the molecular dynamics calculation, the conditions such as the numbers of the respective filler particles 4c and 4s and polymer particles 6a and 6b, the volume of the virtual space V and the temperature of the virtual space V are maintained constant.

As explained, in the polymer calculation step S4b, only the polymer models 5 are dispersed in the virtual space V in advance of the filler models 3. Therefore, preserving the compact cluster of the filler models, the stable arrangement of the polymer models 5 can be obtained.

For example, when the molecular dynamics calculation is made in steps of 0.05[τ] ([τ] is unit of time), if the number of the steps is less than 100, since the total computational time is short, it is different to disperse the polymer models 5 sufficiently. If the number of the steps exceeds 1,000,000, though the computational cost is increased, a good dispersion compatible with the increased computational cost can not be obtained.

Therefore, the number of the steps of about 0.05[τ] is not less than 100, preferably not less than 1000, but not more than 1,000,000, preferably not more than 100,000.

Next, a first judging step S4c is implemented.

In the first judging step S4c, the computer judges whether the dispersion of the polymer models 5 is sufficient or not.

In this embodiment, if the dispersion of the polymer models 5 is judged as being insufficient, then the dispersion of the polymer models 5 is furthered by increasing the number of the steps making the molecular dynamics calculation in the polymer calculation step S4b.

If the dispersion of the polymer models 5 is judged as being sufficient by the computer 1, then the process advances to the next releasing step S4d.

In the releasing step S4d, the filler particles 4 of the filler models 3 are each released.

More specifically, the computer 1 allows the filler particles 4 to change their positional coordinates within the virtual space V in order that the filler models 3 can be moved freely within the virtual space V in the after-mentioned link step S4e and filler-and-polymer calculation step S4f.

Figure 10A:
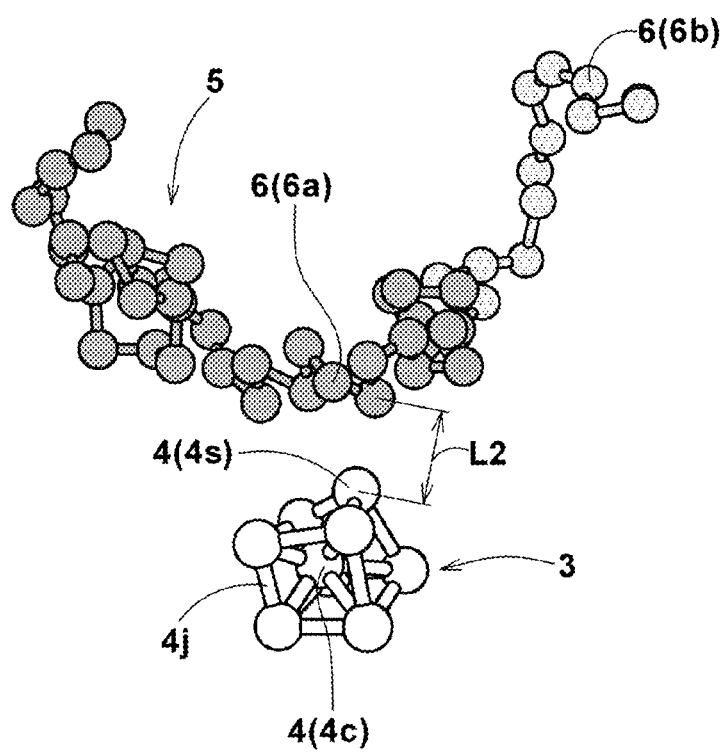
FIGS. 10(a) and 10(b) are diagrams for explaining a link step.
Figure 10B:
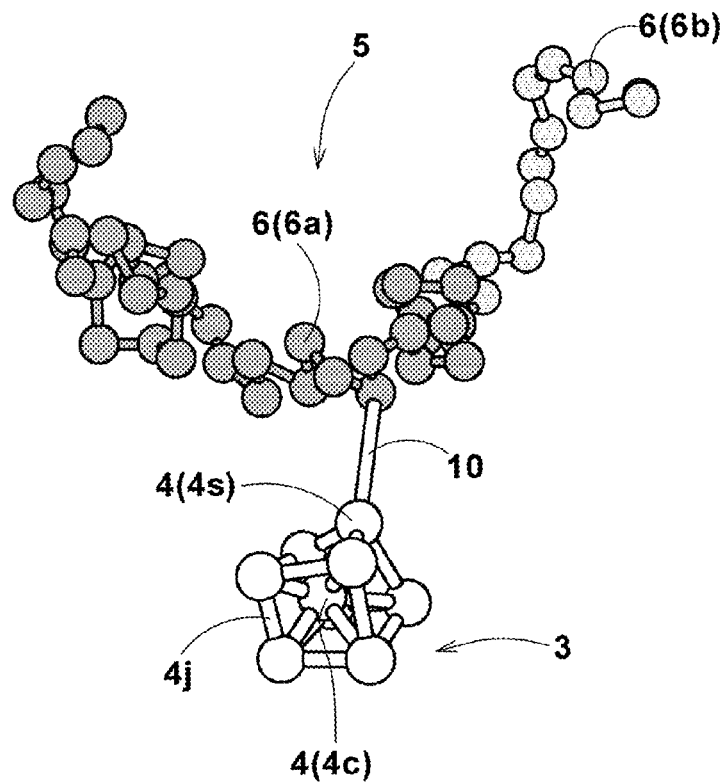

In the link step S4e, as shown in FIGS. 10(a) and 10(b), the filler particles 4, which are approached to less than the predetermined between-particle distance L2 to the polymer particles 6, are linked to the polymer particles 6 by joining chains 10.

The polymer particles 6a and 6b are linked to only the surface filler particles 4s of the filler models 3.

Therefore, in the simulation step, a chemical linkage of the filler and polymer are simulated.

As explained above, since the surface filler particles 4s are linked to the center filler particle 4c to maintain their relative positions to the center filler particle 4c, the positions of the polymer models 5 relative to the filler model 3 can be determined uniquely. Therefore, the sliding movements of the polymer models 5 can be prevented, and the simulation accuracy can be improved.

Preferably, the above-mentioned between-particle distance L2 is set in the range of from 10 to 200% of the cutoff distance $r_c$ (shown in FIG. 7) of the potential related to the surface filler particle 4s.

Next, a filler-and-polymer calculation step S4f is implemented by the computer 1.

In the filler-and-polymer calculation step S4f, a molecular dynamics calculation is made for the filler models 3 and the polymer models 5.

More specifically, assuming that all of the polymer models 5 and filler models 3 follow the classical dynamics, the calculation according to Newton's equation of motion is made during a given time period, and the motion of each of the filler particles 4c and 4s and the polymer particles 6a and 6b is tracked at each time step during the time period.

During the molecular dynamics calculation, the conditions such as the numbers of the respective filler particles 4c and 4s and polymer particles 6a and 6b, the volume of the virtual space V and the temperature of the virtual space V are maintained constant.

Figure 11:
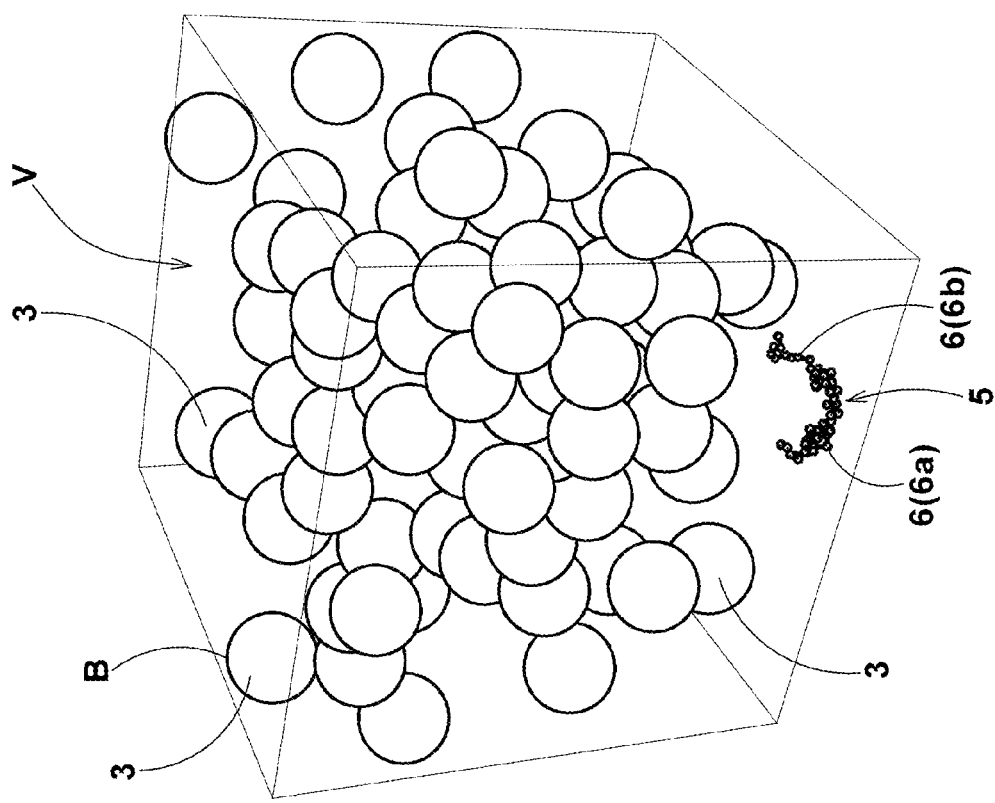
FIG. 11 is a perspective diagram showing the simulation model after the filler-and-polymer calculation step.

Through the filler-and-polymer calculation step S4f, as shown in FIG. 11, the filler models 3 and the polymer models 5 are dispersed in the virtual space V.

In order to effectively disperse the filler models 3 and polymer models 5 in the filler-and-polymer calculation step S4f, when the molecular dynamics calculation is made in steps of 0.05[τ] for example, the number of the steps is preferably not less than 1000, more preferably not less than 5000, but not more than 1,000,000, more preferably not more than 100,000. If the number of the steps is less than 1000, there is a possibility that the filler models 3 and the polymer models 5 can not be fully dispersed. If the number of the steps exceeds 1,000,000, though the computational cost is increased, a good dispersion compatible with the increased computational cost can not be obtained.

Next, a second judging step S4g is implemented, wherein the computer judges whether the dispersion of the filler models 3 and the dispersion of the polymer models 5 are sufficient or not.

In this embodiment, the dispersion of the filler models 3 and the polymer models 5 is judged as being insufficient, then the dispersion of the filler models 3 and the polymer models 5 is furthered by increasing the number of the steps making the molecular dynamics calculation in the filler-and-polymer calculation step S4f.

If the dispersion of the filler models 3 and the polymer models 5 is judged as being sufficient, then the process advances to the next evaluation step S5.

In the evaluation step S5, as shown in FIG. 2, firstly, a radial distribution function computing step S5a is implemented.

In the radial distribution function computing step S5a, a radial distribution function g(r) is computed for the center filler particles 4c of the filler models 3.

Here, the radial distribution function g(r) is a probability density function which figures out the probability (g) that another center filler particle 4c exists at a distance (r) from a center filler particle 4c.

The radial distribution function g(r) is given by the following expression (2):

$$g(r) = \frac{\langle n(r) \rangle}{4\pi r^2 \Delta r \rho}$$

wherein n(r) is the number of particles existing between a distance (r) and a distance (r+Δr) from a center filler particle 4c, in other words, between two concentric spherical surfaces of a radius (r) and radius (r+Δr) whose centers coincide with the center of a center filler particle 4c, <n(r)> is the average of the n(r) across all of the center filler particles 4c during a computational time, and ρ is the number density of the center filler particles 4c in the virtual space V.

Figure 12:
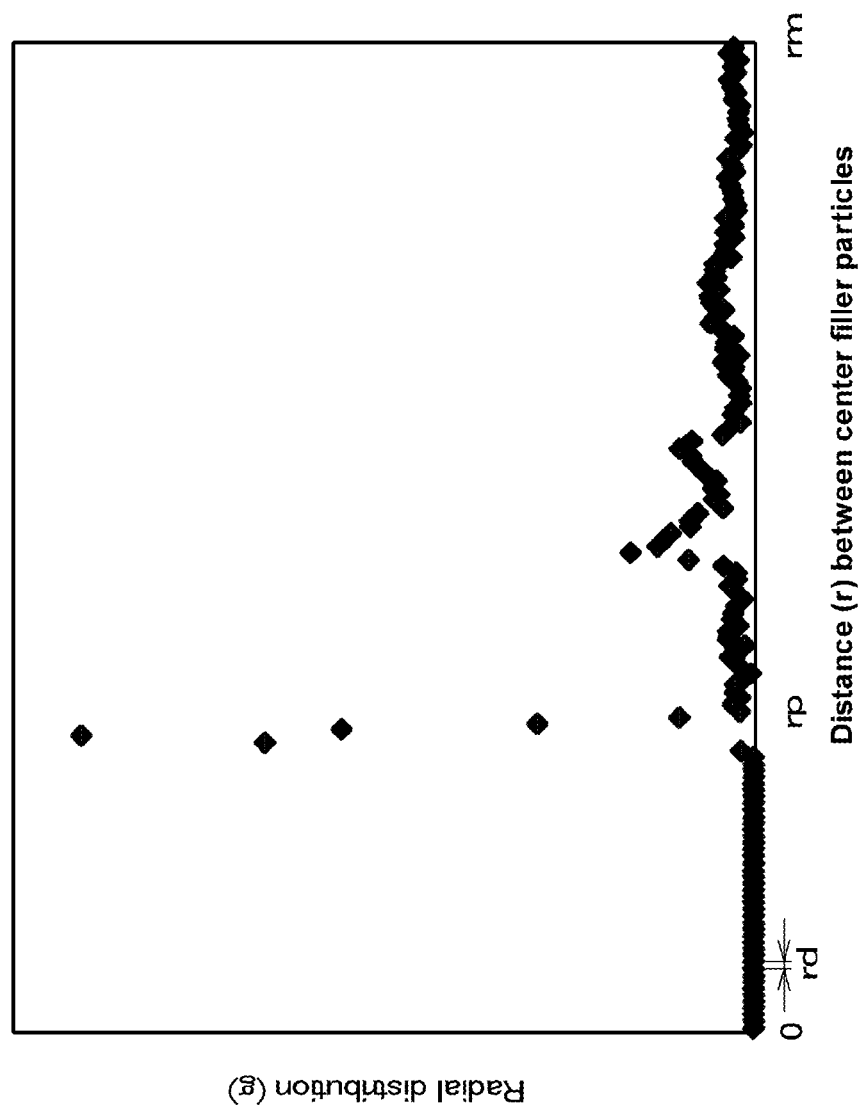
FIG. 12 is a graph of a radial distribution function.
Figure 13A:
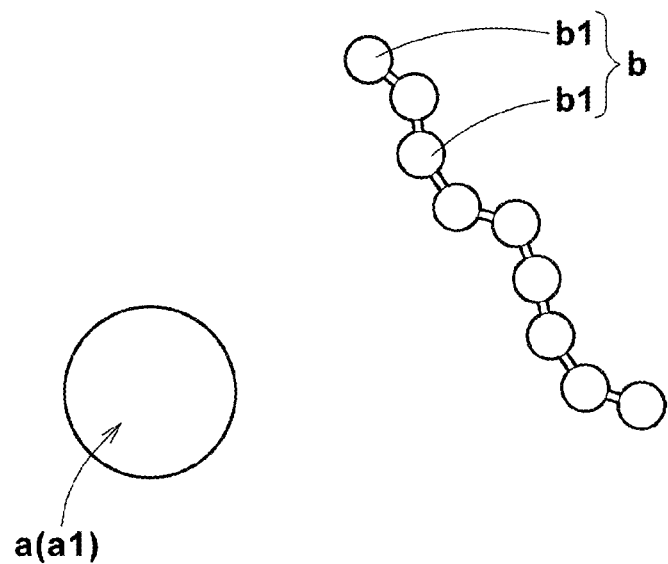
FIG. 13(a) is a diagram showing the known filler model and polymer model.
Figure 13B:
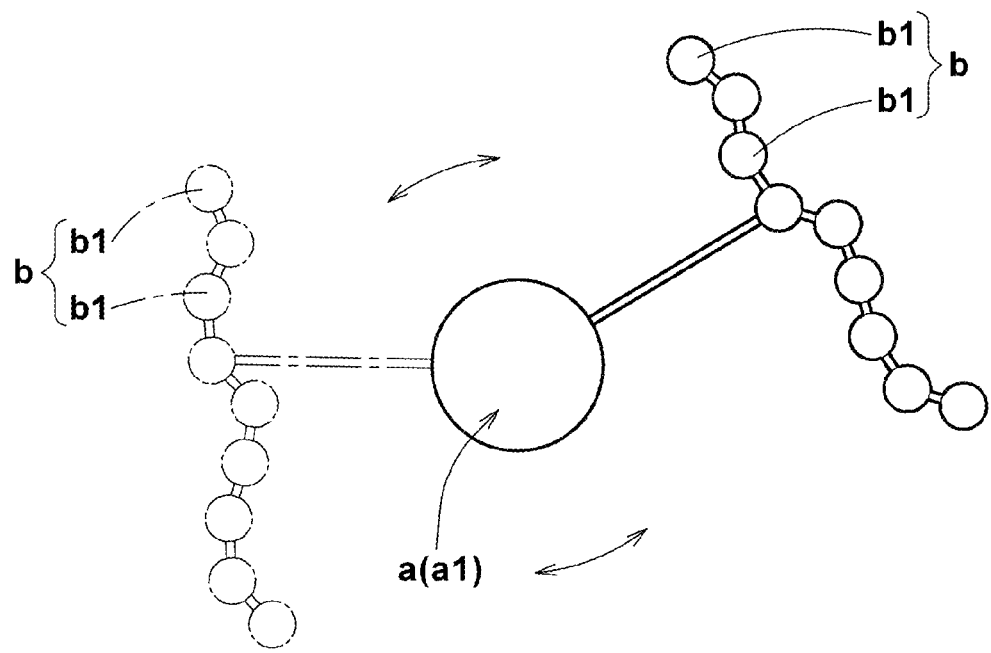
FIG. 13(b) is a diagram for explaining the sliding movement of the known polymer model.

FIG. 12 shows the radial distribution between the center filler particles 4c in this embodiment. From this figure, it can be confirmed that the radial distribution is uniformly widely spread from the maximum distance "rm" close to "rp" at which the radial distribution g(r) becomes peak.

This means that the filler models 3 are evenly distributed in the virtual space V.

In this embodiment, thus, it is possible to know the state of dispersion of the filler models 3 by computing the radial distribution function g(r) only for the center filler particles 4c. Accordingly, it becomes possible to reduce the computational cost.

When computing the radial distribution function, it is desirable that the lower limit of the distance (r) namely the minimum distance (rs) is set to 0, and the upper limit of the distance (r) namely the maximum distance (rm) is set to one half of the length L1 of one side of the virtual space V (shown in FIG. 8). Therefore, it is possible to make accurate evaluations, while inhibiting an excessive increase in the computational cost. In the case that the sides of the virtual space V are not the same length L1, it is desirable that the maximum distance (rm) is set to one half of the length L1 of the shortest side.

It is preferable that, as shown in FIG. 12, the acquisition intervals (rd) of the radial distribution function g(r) correspond to a distance of not more than 1/5 times, more preferably not more than 1/10 times the above-mentioned maximum distance (rm). Therefore, the precision of the results of the radial distribution function g(r) is increased, and it becomes possible to make accurate evaluations.

If the acquisition interval (rd) is too short, the computational cost increases. Therefore, the acquisition intervals (rd) are preferably not less than 1/100 times the maximum distance (rm) and not more than 1/5 times the maximum distance (rm). In the radial distribution shown in FIG. 12, the acquisition intervals (rd) are 1/155 times the maximum distance (rm).

In the evaluation step S5 in this embodiment, then, a judging step S5b is implemented.

In the judging step S5b, the computer judged whether the state of dispersion of the filler models 3 is good or not. More specifically, based on the computational results of the radial distribution function g(r), the computer judges whether the state of dispersion is within the predetermined allowable range or not.

If the dispersion of the filler models 3 is judged as being not good by the computer 1, then the conditions defined for the filler models 3 and polymer models 5 are changed based on the computational results of the radial distribution function g(r), and the simulation is again implemented.

If the dispersion of the filler models 3 is judged as being good by the computer 1, the simulation is ended.

Thus, it is possible to make the right decisions on the conditions capable of surely dispersing the filler models 3.

The invention claimed is:

1. A computerized simulation method for evaluating dispersion of fillers in a high polymer material, comprising
a filler model defining step in which filler models of the fillers are defined, wherein each of the filler models represents filler particles,
a polymer model defining step in which polymer models of the high polymer material are defined, wherein each of the polymer models represents polymer particles,
a condition setting step in which simulation conditions are set,
a simulation step in which a molecular dynamics calculation is made for the polymer models and the filler models placed in a virtual space, and
an evaluation step in which the dispersion of the filler models is evaluated from data obtained in the simulation step by the molecular dynamics calculation,
wherein
the filler particles of each of the filler models are a single center filler particle and at least four surface filler particles of which centers are positioned on a spherical surface of which center coincides with the center of the center filler particle, between the center filler particle and the surface filler particles and also between the surface filler particles, equilibrium lengths are respectively defined, and
the simulation step includes a link step in which the filler particles, which are approached to less than a predetermined between-particle distance to the polymer particles, are linked to the polymer particles under such conditions that the polymer particles can be linked to only the surface filler particles.

2. The method according to claim 1, wherein
between the filler particles and the polymer particles, potentials are defined so that when the distance between the concerned particles is decreased under a predetermined cutoff distance, a mutual interaction occurs therebetween, and
the cutoff distance related to the center filler particle is larger than the sum of the cutoff distance related to the surface filler particle and the radius of the spherical surface.

3. The method according to claim 2, wherein
the condition setting step includes
an initial setup step in which the filler models and the polymer models are placed in the virtual space, and
a compact cluster defining step in which a compact cluster of at least two filler models is formed by approximating the filler models so as to cause a mutual interaction between the filler models.

4. The method according to claim 2, wherein
the evaluation step includes a step of computing a radial distribution function for the center filler particle of each of the filler models.

5. The method according to claim 1, wherein
the evaluation step includes a step of computing a radial distribution function for the center filler particle of each of the filler models.

6. The method according to claim 5, wherein
the shape of the virtual space is a regular hexahedron,
the distance range of the radial distribution function is from zero to one half of the length of one side of the shape of the virtual space, and
acquisition intervals of the radial distribution function correspond to a distance of not more than 1/5 times said one half of the length.

7. The method according to claim 1, wherein
the simulation step includes
a filler movement limiting step in which movement of each of the filler particles is limited,
a polymer calculation step in which a molecular dynamics calculation is made for each of the polymer models, excluding the filler particles,
a releasing step in which the filler particles are released, and
a filler-and-polymer calculation step in which a molecular dynamics calculation is made for the filler models and the polymer models.

8. The method according to claim 7, wherein
in the polymer calculation step, when the molecular dynamics calculation is made in steps of approximate $0.05[\tau]$ ($[\tau]$ is unit of time), the number of the steps is 100 or more.

9. The method according to claim 7, wherein
in the filler-and-polymer calculation step, when the molecular dynamics calculation is made in steps of approximate $0.05[\tau]$ ($[\tau]$ is unit of time), the number of the steps is 1000 or more.

* * * * *